(12) United States Patent
Carter et al.

(10) Patent No.: US 8,845,965 B2
(45) Date of Patent: Sep. 30, 2014

(54) SENSOR

(75) Inventors: Timothy Joseph Nicholas Carter, Sittingbourne (GB); Steven Andrew Ross, Sittingbourne (GB); Timothy Stuart Dwyer, Sittingbourne (GB)

(73) Assignee: Vivacta Ltd., Sittingbourne, Kent (GB)

( * ) Notice: Subject to any disclaimer, the term of this patent is extended or adjusted under 35 U.S.C. 154(b) by 0 days.

(21) Appl. No.: 12/993,747

(22) PCT Filed: Mar. 31, 2009

(86) PCT No.: PCT/GB2009/050313
§ 371 (c)(1),
(2), (4) Date: Mar. 21, 2011

(87) PCT Pub. No.: WO2009/141637
PCT Pub. Date: Nov. 26, 2009

(65) Prior Publication Data
US 2011/0182776 A1    Jul. 28, 2011

Related U.S. Application Data

(60) Provisional application No. 61/055,287, filed on May 22, 2008.

(30) Foreign Application Priority Data

May 21, 2008  (GB) .................................. 0809237.1

(51) Int. Cl.
*G01N 15/06*   (2006.01)
*G01N 33/00*   (2006.01)
*G01N 33/48*   (2006.01)
*G01N 33/543*  (2006.01)
*G01N 29/02*   (2006.01)
*G01N 29/24*   (2006.01)
*G01N 25/48*   (2006.01)

(52) U.S. Cl.
CPC .......... *G01N 33/5438* (2013.01); *G01N 25/482* (2013.01); *G01N 33/54393* (2013.01); *G01N 29/022* (2013.01); *G01N 29/2418* (2013.01)
USPC ........... 422/68.1; 422/50; 422/82.01; 422/81; 436/43; 436/63

(58) Field of Classification Search
CPC ........ G01N 15/06; G01N 33/00; G01N 33/48
USPC ................. 422/50, 68.1, 82.01, 81, 502, 503; 436/43, 63
See application file for complete search history.

(56) References Cited

U.S. PATENT DOCUMENTS

2002/0081570 A1 * 6/2002 Lilien et al. ........................ 435/5

(Continued)

FOREIGN PATENT DOCUMENTS

EP    1536227 A2    6/2005
WO   2004/090512 A1  10/2004

OTHER PUBLICATIONS

Lange, K. et al. "Chemical modification of parylene C coatings for SAW biosensors," Sensors and Actuators B, vol. 125, No. 2, pp. 441-446 (2004).

(Continued)

*Primary Examiner* — Brian J Sines
(74) *Attorney, Agent, or Firm* — Rothwell, Figg, Ernst & Manbeck, P.C.

(57) ABSTRACT

The present application relates to a sensor (1) for use in detecting an analyte comprising: a transducer (10) composed of a pyroelectric or piezoelectric polymer substrate e.g. PVDF (3) and a transparent electrode layer (4) on a surface of the substrate; a layer of parylene (12) on the transparent electrode layer; and a reagent (17) immobilised on the transducer, the reagent having a binding site which is capable of binding the analyte or a derivative of the analyte.

9 Claims, 7 Drawing Sheets

(56) References Cited

U.S. PATENT DOCUMENTS

| | | | |
|---|---|---|---|
| 2005/0003560 A1* | 1/2005 | Zeng et al. | 436/527 |
| 2007/0116733 A1* | 5/2007 | Graneli et al. | 424/423 |
| 2009/0011521 A1* | 1/2009 | Lu et al. | 436/501 |
| 2009/0032401 A1* | 2/2009 | Ronaghi et al. | 204/549 |
| 2010/0033058 A1* | 2/2010 | Lee et al. | 310/323.21 |

OTHER PUBLICATIONS

Lee, J.H., et al., "Microstructure and adhesion of Au deposited on parylene-c substrate with surface modification for potential immunoassay application," IEEE Transactions on Plasma Science, vol. 32, No. 2, pp. 505-509 (2004).

Wright, J.D., et al., "Development of a piezo-optical chemical monitoring system," Sensors and Actuators B, vol. 51, pp. 121-130 (1998).

* cited by examiner

SENSOR

This application is a filing under 35 USC 371 of PCT/GB2009/050313, filed Mar. 31, 2009, which claims priority from GB 0809237.1, filed May 21, 2008 and US 61/055,287, filed May 22, 2008. These prior applications are incorporated herein by reference in their entireties.

The present invention relates to a sensor and in particular to a sensor employing a coated transducer to provide improved sensitivity and reproducibility.

The monitoring of analytes in solution, such as biologically important compounds in a bioassay, e.g. an immunoassay, has a broad applicability. An immunoassay is a test which measures the presence or more usually the concentration of an analyte in a biological fluid. It typically involves the specific binding of an antigen to an antibody. The antibody can be polyclonal or monoclonal, monoclonal antibodies having several benefits, including reproducibility of manufacture and containment of binding to one epitope of an analyte. In order to provide a quantifiable measure of the concentration of the analyte, the response is compared to standard samples of known concentration. The concentration of the antibody or antigen may be determined by a variety of methods, although one of the most common is to label either the antigen or antibody and detect the presence of the label.

Immunoassays can be competitive or non-competitive. In a competitive immunoassay, the antigen in the unknown sample competes with labelled antigen to bind to antibodies, which are typically immobilised on a solid phase. The amount of labelled antigen bound to the antibody site is then measured, usually by separating and measuring the labelled antigen bound to the solid phase. Clearly the response will be inversely proportional to the concentration of antigen in the unknown sample. In an analogous assay principle, labelled antibody in solution competes with antigen immobilised on a solid phase and that present in the sample, giving a similar inverse proportionality. In a non-competitive immunoassay, also referred to as an immunometric assay, the antigen in the unknown sample binds to an excess of immobilised antibodies (the "capture" antibodies) and the amount of bound antigen is measured. Unlike the competitive method, the results of the non-competitive method will be directly proportional to the concentration of the antigen. In a so-called "two-site" immunometric assay, also termed a "sandwich assay", the antigen is bound to the capture antibody site, and then labelled antibody is introduced which binds to the antigen bound to the capture antibody. The amount of labelled antibody at the site is then measured.

In a typical sandwich immunoassay, an antibody specific for an antigen of interest is attached to a polymeric support such as a sheet of polystyrene. A drop of the sample to be tested, e.g. a cell extract or a sample of serum or urine, is laid on the sheet, which is washed after formation of the antibody-antigen complex. Antibody specific for a different site on the antigen is then added, and the support is again washed. This second antibody carries a label (the labelled reporter) so that it can be detected with high sensitivity. The amount of second antibody bound to the sheet is proportional to the quantity of antigen in the sample. This assay and other variations on this type of assay are well known, see, for example, "The Immunoassay Handbook, 2nd Ed." David Wild, Ed., Nature Publishing Group, 2001.

A wide variety of analytical and diagnostic devices are available for performing immunoassays. The device contains a sensor which selectively binds the analyte of interest and the binding event is then quantified. Many devices employ a reagent on the sensor which undergoes a detectable change, e.g. a colour change, in the presence of the analyte being detected.

WO 90/13017 discloses a pyroelectric or other thermoelectric transducer element in a strip form. Thin film electrodes are provided and one or more reagents are deposited on the transducer surface. The reagent undergoes a selective colorimetric change when it comes into contact with the species being detected. The device is then typically inserted into a detector where the transducer is illuminated usually from below by an LED light source and light absorption by the reagent is detected as microscopic heating at the transducer surface. The electrical signal output from the transducer is processed to derive the concentration of the species being detected.

The system of WO 90/13017 provides for the analysis of species which produce a colour change in the reagent on reaction or combination with the reagent. For example, reagents include pH and heavy metal indicator dyes, reagents (e.g. o-cresol in ammoniacal copper solution) for detecting aminophenol in a paracetamol assay, and a tetrazolium dye for detecting an oxidoreductase enzyme in an enzyme-linked immuno-sorbant assay (ELISA). However, while this system is useful in certain applications, it has been considered suitable only for analysis where the species being analysed generates a colour change in the reagent since it is the reagent which is located on the surface of the transducer. Therefore, this system cannot be applied to the analysis of species which do not cause a colour change in the reagent or when the colour change is not on the surface of the transducer.

WO 2004/090512 discloses a device based on the technology disclosed in WO 90/13017, but relies on the finding that energy generated by non-radiative decay in a reagent on irradiation with electromagnetic radiation may be detected by a transducer even when the reagent is not in contact with the transducer, and that the time delay between the irradiation with electromagnetic radiation and the electrical signal produced by the transducer is a function of the distance of the reagent from the surface of the film. This finding provided a device capable of "depth profiling" which allows the device to distinguish between an analyte bound to the surface of the transducer and an analyte in the bulk liquid. This application therefore discloses a device which is able to be used in assays, typically bioassays, without having to carry out a separate washing step between carrying out a binding event and detecting the results of that event.

The devices disclosed in WO 90/13017 and WO 2004/090512 have found wide applicability and further variations are disclosed in WO 2006/079795, WO 2007/107716, WO 2007/129064 and WO 2007/141581.

Figure 1:
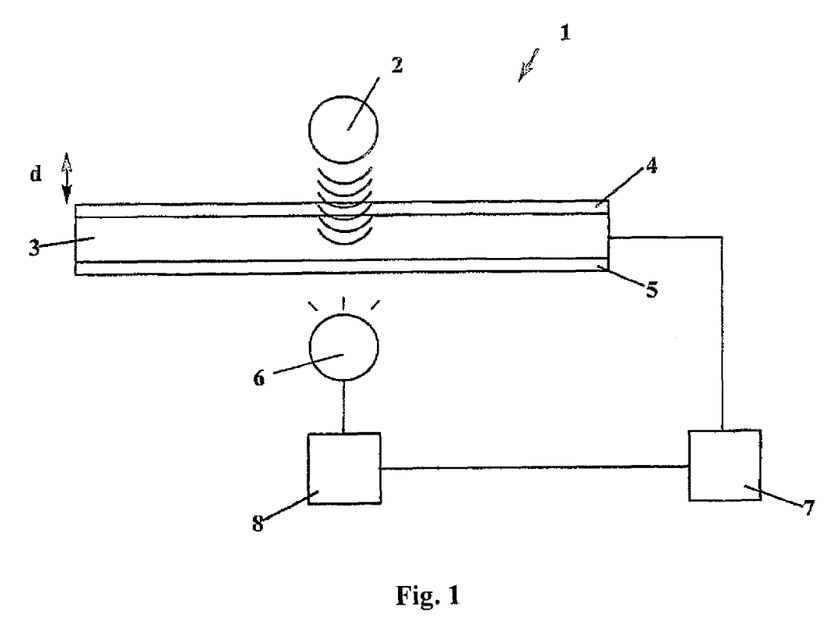
FIG. 1 shows a device according to WO 2004/090512.

A common theme is that the sensor includes a transducer having a pyroelectric or piezoelectric element and electrodes which is capable of transducing a change in energy to an electrical signal. FIG. 1 shows the principle of this chemical sensing device 1. The device 1 relies on heat generation in a substance 2 on irradiation of the substance 2 with electromagnetic radiation. The device 1 comprises a pyroelectric or piezoelectric transducer 3 having electrode coatings 4,5. The transducer 3 is preferably a film, e.g. a poled polyvinylidene fluoride (PVDF) film. The electrode coatings 4,5 are preferably formed from indium tin oxide (ITO) having a thickness of about 35 nm, although almost any thickness is possible from a lower limit of 1 nm below which the electrical conductivity is too low and an upper limit of 100 nm above which the optical transmission is too low (it should not be less than 95% T). A substance 2 is held on or proximal to the transducer 3 using any suitable technique, shown here attached to the upper electrode coating 4. The reagent may be in any suitable form and a plurality of reagents may be deposited. Preferably, the substance 2 is adsorbed on to the upper electrode, e.g. covalently coupled or bound via intermolecular forces such as ionic bonds, hydrogen bonding or van der Waal's forces.

A key feature of this device is that the substance 2 generates heat when irradiated by a source of electromagnetic radiation 6, such as light, preferably visible light. The light source may be, for example, an LED. The light source 6 illuminates the substance 2 with light of the appropriate wavelength (e.g. a complementary colour). Although not wishing to be bound by theory, it is believed that the substance 2 absorbs the light to generate an excited state which then undergoes non-radiative decay thereby generating energy, indicated by the curved lines in FIG. 1. This energy is primarily in the form of heat (i.e. thermal motion in the environment) although other forms of energy, e.g. a shock wave, may also be generated. The energy is, however, detected by the transducer and converted into an electrical signal.

The device is calibrated for the particular reagent being measured and hence the precise form of the energy generated by the non-radiative decay does not need to be determined. Unless otherwise specified the term "heat" is used herein to mean the energy generated by non-radiative decay. The light source 6 is positioned so as to illuminate the substance 2. Preferably, the light source 6 is positioned substantially perpendicular to the transducer 3 and electrodes 4,5 and the substance 2 is illuminated through the transducer 3 and electrodes 4,5. The light source may be an internal light source within the transducer in which the light source is a guided wave system. The wave guide may be the transducer itself or the wave guide may be an additional layer attached to the transducer. The wavelength of illumination depends on the label used; for example, for 40 nm gold labels the preferred wavelength is 525 nm and for carbon labels the preferred wavelength is 650 nm.

The energy generated by the substance 2 is detected by the transducer 3 and converted into an electrical signal. The electrical signal is detected by a detector 7. The light source 6 and the detector 7 are both under the control of the controller 8.

In one embodiment, the light source 6 generates a series of pulses of light (the term "light" used herein means any form of electromagnetic radiation unless a specific wavelength is mentioned) which is termed "chopped light". In principle, a single flash of light, i.e. one pulse of electromagnetic radiation, would suffice to generate a signal from the transducer 3. However, in order to obtain a reproducible signal, a plurality of flashes of light are used which in practice requires chopped light. The frequency at which the pulses of electromagnetic radiation are applied may be varied. At the lower limit, the time delay between the pulses must be sufficient for the time delay between each pulse and the generation of an electrical signal to be determined. At the upper limit, the time delay between each pulse must not be so large that the period taken to record the data becomes unreasonably extended. Preferably, the frequency of the pulses is from 2-50 Hz, more preferably 5-15 Hz and most preferably 10 Hz. This corresponds to a time delay between pulses of 20-500 ms, 66-200 ms and 100 ms, respectively. In addition, the so-called "mark-space" ratio, i.e. the ratio of on signal to off signal is preferably one although other ratios may be used to advantage in certain situations. Sources of electromagnetic radiation which produce chopped light with different frequencies of chopping or different mark-space ratios are known in the art. The detector 7 determines the time delay (or "correlation delay") between each pulse of light from light source 6 and the corresponding electrical signal detected by detector 7 from transducer 3. This time delay is a function of the distance, d.

Any method for determining the time delay between each pulse of light and the corresponding electrical signal which provides reproducible results may be used. Preferably, the time delay is measured from the start of each pulse of light to the point at which a maximum in the electrical signal corresponding to the absorption of heat is detected as by detector 7.

Thus substance 2 may be separated from the transducer surface and a signal may still be detected. Moreover, not only is the signal detectable through an intervening medium capable of transmitting energy to the transducer 3, but different distances, d, may be distinguished (this has been termed "depth profiling") and that the intensity of the signal received is proportional to the concentration of the substance 2 at the particular distance, d, from the surface of the transducer 3.

However, there remains a need to continue to seek for improved signal strength and reproducibility.

Accordingly, the present invention provides a sensor for use in detecting an analyte comprising:
a transducer composed of a pyroelectric or piezoelectric polymer substrate and a transparent electrode layer on a surface of the substrate;
a layer of parylene on the transparent electrode layer; and
a reagent immobilised on the transducer, the reagent having a binding site which is capable of binding the analyte or a derivative of the analyte.

The parylene layer provides an improved surface for the subsequent attachment of the reagent.

The present invention will now be described with reference to the drawings, in which.

Figure 2:
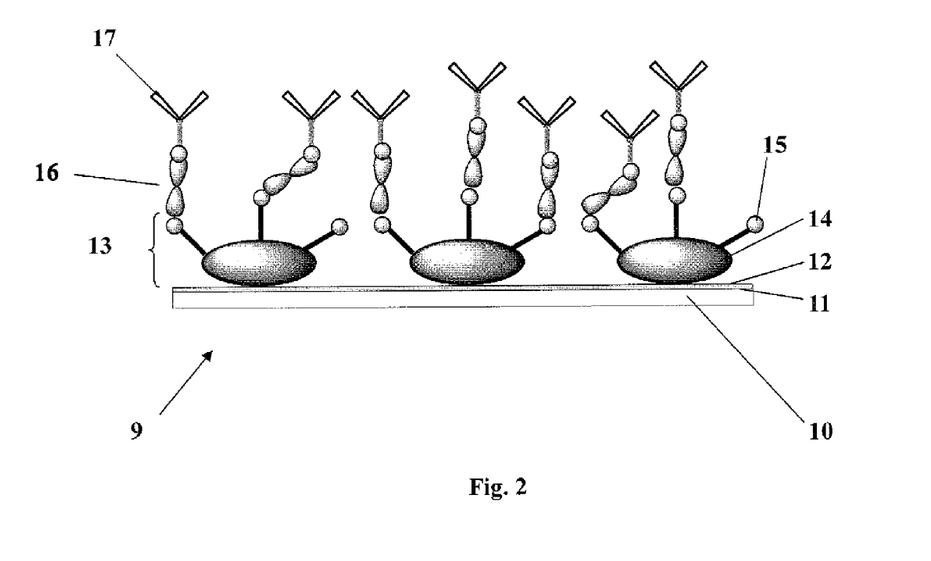
FIGS. 2 and 3 show schematic representations of the sensor of the present invention.

It has been found that the intensity and the reproducibility of the signal obtained from the device described with reference to FIG. 1 can be improved by coating the surface of the transducer with a layer of parylene (see FIG. 2). FIG. 2 shows a sensor 9 having a transducer 10. The transducer 10 is composed of a pyroelectric or piezoelectric polymer substrate and a transparent electrode layer on a surface of the substrate of the type described hereinabove with reference to FIG. 1.

The substrate is formed from a pyroelectric or piezoelectric polymer, such as a polyvinylidene fluoride film. Polyvinylidene fluoride is a well-known pyroelectric/piezoelectric polymer. The surface of the substrate is coated in a transparent electrode layer. By transparent is meant that the layer is transparent at least at the wavelength of electromagnetic radiation used in the detection of the binding event between the analyte and reagent. This layer is preferably composed of indium-tin oxide (ITO). In a preferred embodiment, the transducer 10 is an ITO-coated polyvinylidene fluoride film.

The transducer 10 is shown in FIG. 2 as a planar transducer and the transducer 10 has a first surface 11 which is coated with a layer of parylene 12. The other surfaces of the transducer 10 could also be coated, for example where both surfaces come into contact with the sample (not shown).

The parylene layer 12 is further coated with a layer of protein 13. The protein is shown as a biotinylated hydrophobic protein of types well known in the art. The protein is shown diagrammatically in FIG. 2 with the protein backbone 14 attached to the transducer 10 and the biotin moieties 15 exposed. The transducer 10 further comprises a streptavidin layer 16 which coats the protein layer 13. The streptavidin layer 16 has the reagent 17 bound thereto.

The immobilised reagent 17 is capable of binding to the analyte being detected or a derivative of the analyte. The binding event is then detected as described hereinabove. The reagent 17 is preferably an antibody raised to bind selectively to the analyte or derivative of the analyte when the sample is introduced.

Figure 3:
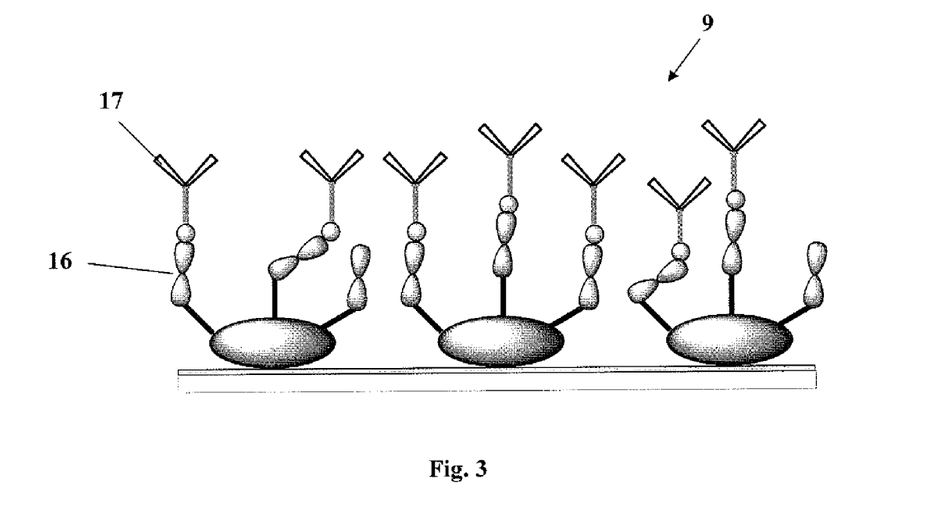

FIG. 3 shows a sensor 9 similar to that described with reference to FIG. 2, except that the parylene layer 12 has a polystreptavidin layer 16 attached directly thereto. The biotinylated antibody 17 is then bound to the polystreptavidin layer 16.

The surface may also be covered by further coatings to stabilise the surface, e.g. Stabilcoat from SurModics Inc, Eden Prairie, Minn., USA (not shown).

Parylene is a generic term which describes a class of polymers which are derived from [2,2]paracyclophanes. Generally, parylene is not prepolymerised prior to coating, but rather is deposited on the surface to be coated by a pyrolitic deposition process. This process involves vaporisation of the [2,2]paracyclophane which is then pyrolitically cleaved to form a diradical monomer, followed by deposition of the monomer upon the substrate to be coated to form the polymer. The cleavage is promoted by the internal strain within the [2,2]paracyclophane. The vaporisation conditions will depend on the [2,2]paracyclophane used, but is typically conducted at about 50-200° C. and 100-200 Nm$^{-2}$, e.g. 150° C. and 135 Nm$^{-2}$. Pyrolysis is typically at a temperature of 400-700° C. and 40-100 Nm$^{-2}$, e.g. 680° C. and 65 Nm$^{-2}$. The deposition may be carried out at room temperature to 75° C. and 5-50 Nm$^{-2}$, e.g. 35° C. and 15 Nm$^{-2}$. The process may be summarised by the following scheme (using parylene C):

Parylenes used in the present invention are obtainable from [2,2]paracyclophanes typically having the following structure:

wherein
aryl represents an aromatic carbocyclic or heterocyclic ring, such as phenylene (preferably 1,4-phenylene), naphthalene, pyridine, etc which may be substituted with halogen; amino; $C_1$-$C_{10}$ alkyl optionally substituted with halogen, preferably $C_1$-$C_5$ alkyl optionally substituted with halogen; $C_3$-$C_{10}$ cycloalkyl optionally substituted with halogen, preferably $C_3$-$C_7$ cycloalkyl optionally substituted with halogen; $C_2$-$C_{10}$ alkylene optionally substituted with halogen, preferably $C_1$-$C_5$ alkyl optionally substituted with halogen; or $C_2$-$C_{10}$ alkylyne optionally substituted with halogen, preferably $C_2$-$C_{10}$ alkylyne optionally substituted with halogen; and $A^1$ and $A^2$, which may the same or different represent: hydrogen; halogen; amino; $C_1$-$C_{10}$ alkyl optionally substituted with halogen, preferably $C_1$-$C_5$ alkyl optionally substituted with halogen; $C_3$-$C_{10}$ cycloalkyl optionally substituted with halogen, preferably $C_3$-$C_7$ cycloalkyl optionally substituted with halogen; $C_2$-$C_{10}$ alkylene optionally substituted with halogen, preferably $C_1$-$C_5$ alkyl optionally substituted with halogen; or $C_2$-$C_{10}$ alkylyne optionally substituted with halogen, preferably $C_2$-$C_{10}$ alkylyne optionally substituted with halogen.

Preferably, the parylenes according to the invention are obtainable from [2,2]paracyclophanes having the following structure:

wherein $A^1$ and $A^2$ are as defined above and $S^1$, $S^2$, $S^3$ and $S^4$, which may the same or different, represent: hydrogen; halogen; amino; $C_1$-$C_{10}$ alkyl optionally substituted with halogen, preferably $C_1$-$C_5$ alkyl optionally substituted with halogen; $C_3$-$C_{10}$ cycloalkyl optionally substituted with halogen, preferably $C_3$-$C_7$ cycloalkyl optionally substituted with halogen; $C_2$-$C_{10}$ alkylene optionally substituted with halogen, preferably $C_1$-$C_5$ alkyl optionally substituted with halogen; or $C_2$-$C_{10}$ alkylyne optionally substituted with halogen, preferably $C_2$-$C_{10}$ alkylyne optionally substituted with halogen.

More preferably $A^1$, $A^2$, $S^1$, $S^2$, $S^3$ and $S^4$, which may be the same or different, represent hydrogen or halogen. Halogen is preferably fluorine or chlorine.

Specific examples of [2,2]paracyclophanes from which the parylene used in the present invention is obtainable include:

As will be apparent form the discussion hereinabove, the resultant parylene polymer as used in the present invention is a polymer has the structure as follows:

wherein aryl, $A^1$ and $A^2$ are as defined above.

Once deposited, the parylene cannot be readily removed from the substrate. This, combined with the low solubility of parylene, makes deposited parylene difficult to characterise using conventional solution-phase techniques. Accordingly, the degree of polymerisation of the parylene is typically determined by the length of time to which the transducer is exposed to the parylene monomers and this in turn influences the thickness of the parylene layer. The parylene layer of the present invention preferably has a thickness of 10 nm to 100 μm, more preferably 100 nm to 10 μm and most preferably 250 nm to 1 μm. If the parylene layer is too thick, the thermal energy does not adequately reach the transducer and if it is too thin, the layer is fragile and also has a tendency to form holes.

Preferably the parylene used in the present invention has a structure as follows:

wherein $A^1$, $A^2$, $S^1$, $S^2$, $S^3$ and $S^4$ are as defined above.

Particularly preferably $A^1$, $A^2$, $S^1$, $S^2$, $S^3$ and $S^4$, which may be the same or different, represent hydrogen or halogen.

Specific examples of parylenes which may be used in the present invention include the following:

Parylene C is particularly preferred.

A layer of protein is preferably incorporated between the parylene layer and the immobilised reagent. The protein layer assists in tethering the reagent to the surface of the transducer, i.e. to the parylene layer. The protein is typically adsorbed on the parylene layer by non-covalent interactions, principally hydrophobic interactions such as van der Waals forces. The protein may be a natural or synthetic polypeptide. The protein will be sufficiently hydrophobic to bind non-covalently to the parylene layer. This may be achieved by incorporating hydrophobic regions in the protein. Where the protein contains both hydrophobic and hydrophobic regions, the protein can faun a tertiary structure which allows the hydrophobic regions to bind to the parylene layer, and the hydrophobic regions to face away from the parylene layer. In this position, the hydrophobic regions can be used to bind to the reagent.

Examples of suitable proteins include $\alpha_2$-macroglobulin (MW 820,000), bovine serum albumin/human serum albumin (MW about 70,000), egg albumin, $\alpha_2$ HS-glycoprotein (MW about 49,000), $\beta_{1c}/\beta_{1a}$-globulin, immunoglobulin (MW about 150,000) and transferrin (MW about 90,000).

When human serum albumin or $\alpha_2$ HS-glycoprotein are used, they are preferably rendered hydrophobic and should be treated to produce a polymeric molecule with a higher molecular weight. When transferrin is used, cross-linking suffices to render this substance useful in the present invention. When $\alpha_2$-macroglobulin is used, the molecule only needs to be rendered hydrophobic. Proteins which are suitable without pre-treatment include, for example, β-lipoproteins (MW about 3.2 million) and $\alpha_2$-lipoproteins (MW about 5-20 million).

Hydrophobing can take place, for example, by the use of heat, treatment with acids, denaturing agents and/or chaotropic ions and/or by chemical coupling with a hydrophobic compound. Increasing of the molecular weight can take place, for example, by the use of heat, treatment with acids, denaturing agents and/or chaotropic ions and/or by cross-linking with a bi- or polyfunctional protein reagent. The treatment is carried out until a protein polymer is obtained with a molecular weight of 500,000 or more. It is especially preferred to use a protein polymer with a molecular weight of from 100,000 to 20 million, more preferably 500,000 to 5 million.

When cross-linking is required, the hydrophobing can be carried out before, during or after the cross-linking. Temperatures of 40-95° C. over 1 minute to 10 hours may be used for hydrophobing by heating, for example as described in Biochem. Biophys. Acta 1980, 624, 13-20. As acids, there are used, for example, acetic acid, propionic acid, lactic acid or hydrochloric acid. The usual concentrations are 1 to 100 mmol/L with a period of action of from 10 minutes to 16 hours. Suitable chaotropic ions include, for example, thiocyanate, iodide, fluoride, bromide, perchlorate and sulfate. Suitable denaturing agents include, for example, guanidine hydrochloride and urea. Concentrations of 10 mmol/L to 6 mol/L are usually used. For the derivatisation of hydrophobic compounds, there are preferably used soluble fatty acids, lipids in low and high molecular weight form, as well as synthetic polymers, such as polypropylene glycol, or soluble copolymers of polystyrene. The derivatisation takes place according to well known methods. Cross-linking by way of bi- and polyfunctional compounds is carried out with known protein binding reagents. These are compounds which contain at least two functional groups, which can be the same or different and can react via these functional groups with functional groups of proteins. Compounds are preferably used which consist of an alkyl chain on the ends of which are present, for example, succinimide, maleimide and/or aldehyde groups. The protein is cross-linked in the usual manner with the bi- or polyfunctional compounds by reacting together the soluble protein and the bi- or polyfunctional compound. For hydrophobing and/or cross-linking, there are preferably used precursor proteins with a molecular weight of from 10,000 to 700,000, bovine serum albumin, lipase and immune γ-globulin being especially preferred. See U.S. Pat. No. 5,061,640 for further details.

The present invention further provides a method of preparing a sensor, comprising the steps of providing a transducer composed of a pyroelectric or piezoelectric polymer substrate and a transparent electrode layer on a surface of the substrate, coating the transparent electrode layer with parylene by vapour deposition of parylene monomers on to the substrate, attaching a receptor to the transducer. Preferably the parylene layer is treated with a protein prior to the step of attaching a receptor to the parylene layer. The sensor deposition may be monitored using a quartz microbalance to control the amount of material deposited.

It is believed that the treatment of the surface of the substrate with parylene results in a more continuous protein coating compared to the untreated surface. This in turn leads to a more intense signal and greater reproducibility between measurements. This has been investigated using XPS (x-ray photoelectron spectroscopy). In XPS, the surface of the substrate is irradiated with x-rays causing electrons to be emitted from atoms on the surface of the substrate. The emitted electrons have a characteristic energy depending upon the type of atom and orbital from which they have been emitted. The technique is therefore used to determine the chemical nature of the surface of the film.

Figure 4:
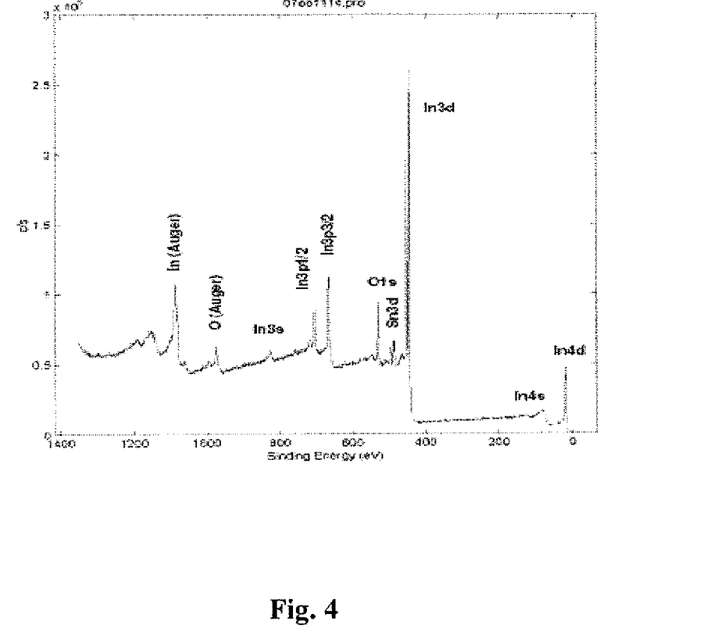
FIGS. 4-6 show XPS spectra of substrates with (FIG. 6) and without (FIGS. 4 and 5) a parylene layer.
Figure 5:
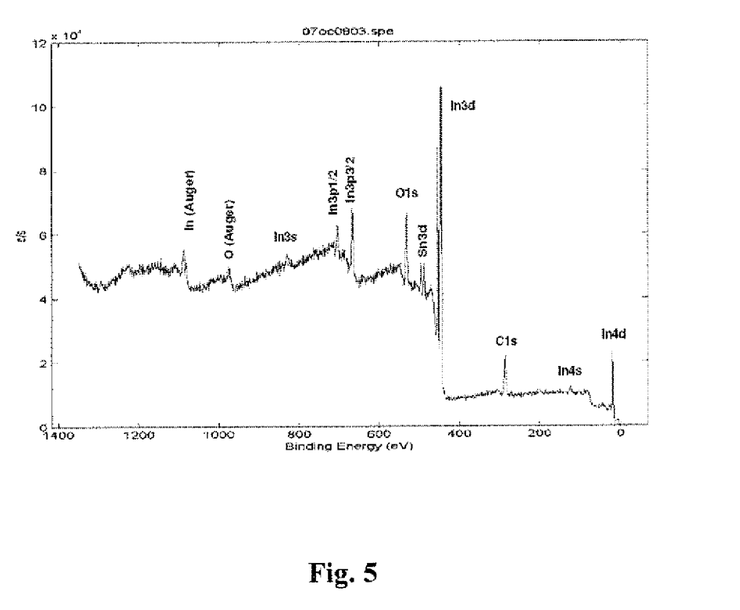
Figure 6:
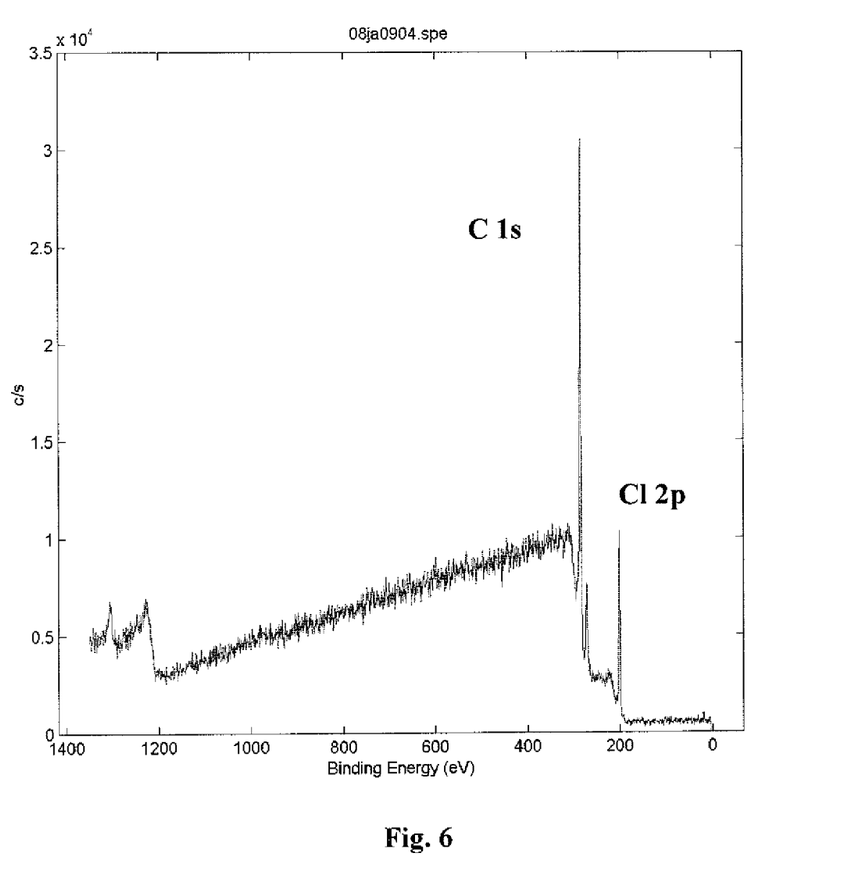

FIG. 4 shows an XPS spectrum of an ITO-coated PVDF film after cleaning by plasma etching, exhibiting the expected peaks for indium, tin and oxygen. FIG. 5 shows the film following subsequent exposure to the atmosphere for several days. A characteristic peak just under 300 eV shows the presence of carbon atoms, in addition to the expected peaks for indium, tin and oxygen. It is believed that the proteins preferentially attach to regions of the substrate which have become contaminated with carbon-containing species, such as atmospheric VOCs, although there is little control on VOCs being deposited on the film surface. FIG. 6 shows an XPS spectrum of the same substrate coated with parylene C. Large peaks for carbon and chlorine are observed in the ratio expected for the parylene C. These data are also summarised in the following table.

TABLE

Elemental surface composition of clean ITO, contaminated ITO, and parylene C-coated ITO piezofilm.

| Elemental composition | Plasma-etched ITO | Contaminated ITO | Parylene C |
|---|---|---|---|
| Carbon % | 0 | 39.2 | 86.1 |
| Oxygen % | 53.5 | 38.2 | 1.5 |
| Indium % | 43.1 | 20.5 | 0.0 |
| Tin % | 3.4 | 2.0 | 0.0 |
| Chlorine % | 0.0 | 0.0 | 11.8 |

Figure 7:
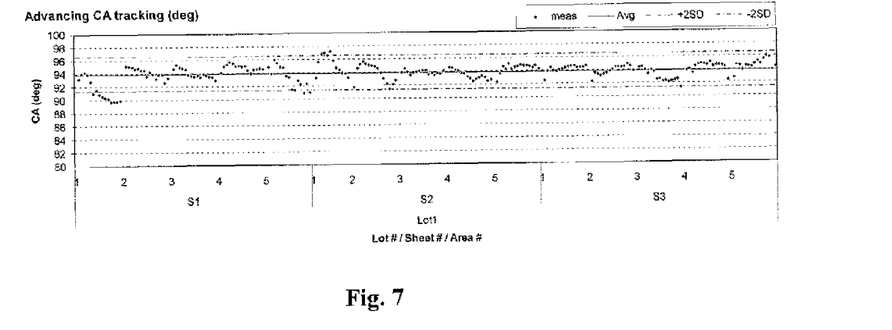
FIG. 7 shows graphically the advancing contact angle measured over different areas of different sheets of parylene C-coated PVDF/ITO.

It is believed that a continuous coating of parylene facilitates binding of proteins to the surface of the substrate. Accordingly, it is preferred that the sensor of the present invention further comprising a protein layer between the parylene layer and the reagent. Parylene also produces a suitably thin film with lower variability in the thickness compared to, say, a dip-coated polystyrene film, which has been demonstrated by measuring light interference patterns from the parylene film. Additionally, a water drop contact angle of around 95° (with little variation) is near optimum for adsorption of hydrophobic proteins and this is demonstrated by the advancing contact angle measured over different areas of different sheets of parylene C-coated PVDF/ITO as shown in FIG. 7. FIG. 7 shows an average water contact angle of 93.9±1.3° (1 standard deviation). The measurement was carried out by the dynamic sessile drop method according to ISO 15989:2004.

In a preferred embodiment, the sensor 9 of the present invention is incorporated into the device described hereinabove with reference to FIG. 1.

Figure 8:
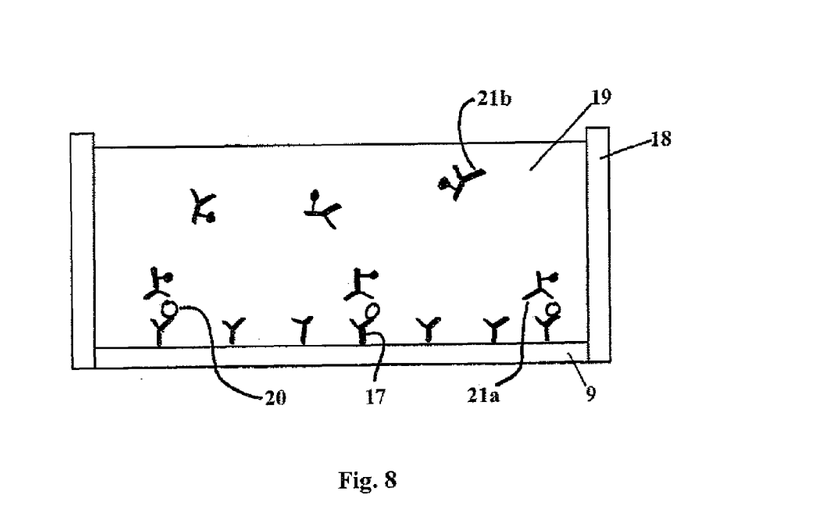
FIG. 8 shows a sample chamber containing the sensor of the present invention.

FIG. 8 shows a typical capture antibody assay using the sensor 9 of the present invention. The sensor 9 of the present invention further includes a well 18 for holding a liquid 19 containing an analyte 20 dissolved or suspended therein. The transducer is integral with the chamber, i.e. the well. The sensor 9 includes a reagent, i.e. antibody 17, attached thereto. The sensor further comprises a source of electromagnetic radiation, and a detector for detecting the electrical signal (not shown) which is described hereinabove with reference to FIG. 1.

In use, the well 18 is filled with liquid 19 (or any fluid) containing the analyte 20. The analyte 20 then binds to antibody 17. Additional labelled antibody 21 is added to the liquid and a sandwich complex is formed between the bound antibody 17, the analyte 20 and the labelled antibody 21. Alternatively the additional labelled antibody 21 can be pre-mixed with the liquid, the end result being the same. An excess of labelled antibody 21 is added so that all of the bound analyte 20 forms a sandwich complex. The sample therefore contains bound labelled antibody 21a and unbound labelled antibody 21b free in solution.

During or following formation of the sandwich complex, the sample is irradiated using a series of pulses of electromagnetic radiation, such as light. The time delay between each pulse and the generation of an electrical signal by the transducer 3 is detected by a detector. The appropriate time delay is selected to measure only the heat generated by the bound labelled antibody 21a. Since the time delay is a function of the distance of the label from the transducer 3, the bound labelled antibody 21a may be distinguished from the unbound labelled antibody 21b.

The label may be any material which is capable of interacting with the electromagnetic radiation generated by the radiation source to generate energy by non-radiative decay. Preferably the label is selected from, but not limited to, a carbon particle, a coloured-polymer particle (e.g. coloured latex), a dye molecule, an enzyme, a fluorescent molecule, a metal (e.g. gold) particle, a haemoglobin molecule, a magnetic particle, a nanoparticle having a non-conducting core material and at least one metal shell layer, a red blood cell, and combinations thereof.

In the case of a magnetic particle, the electromagnetic radiation is radio frequency radiation. All of the other labels mentioned hereinabove employ light, which can include IR or UV radiation. Preferably the label is a gold particle or a carbon particle. Carbon particles have benefits in that they absorb essentially uniformly at all wavelengths of interest and are much less dense than most metallic particles minimising their sedimentation during the assay. Gold particles are commercially available or may be prepared using known methods (see for example G. Frens, Nature 1973, 241, 20-22). For a more detailed explanation of the nanoparticle label see U.S. Pat. No. 6,344,272 and WO 2007/141581. Carbon particles are commercially available, for example, from Degussa, Essen, Germany and methods for their conjugation with proteins and small molecules are known in the art, for example, by Van Doom et al. (U.S. Pat. No. 5,641,689)

Preferably, the present invention uses a particle having a particle size of 20 to 1,000 nm, more preferably 100 to 500 inn. By particle size is meant the diameter of the particle at its widest point.

The label is proximal to the transducer when the binding event has occurred. That is, the label is sufficiently close to the surface of the transducer for the transducer to be able to detect the energy generated by the label on irradiation of the sample. The actual distance between the label and the surface of the transducer will, however, depend on a number of variables, such as the size and nature of the label, the size and nature of the first and second antibodies and the analyte, the nature of the sample medium, and the nature of the electromagnetic radiation and the corresponding setting of the detector. With regard to the nature of the electromagnetic radiation, the sensor of the present invention may include a radiation source which is adapted to generate a series of pulses of electromagnetic radiation and the detector is adapted to determine the time delay between each pulse of electromagnetic radiation from the radiation source and the generation of the electric signal thereby allowing a precise determination of the position of the label with respect to the transducer as discussed with reference to FIG. 1.

The reagent is preferably an antibody, although other reagents could be used. As alternatives to antibody-antigen reactions, the reagent and analyte may be a first and second nucleic acid where the first and second nucleic acids are complementary, or a reagent containing avidin or derivatives thereof and an analyte containing biotin or derivatives thereof, or vice versa. The system is also not limited to biological assays and may be applied, for example, to the detection of heavy metals in water. The system also need not be limited to liquids and any fluid system may be used, e.g. the detection of enzymes, cells and viruses etc. in the air.

The unknown sample is expected to contain the analyte, but of course the assay of the present invention may be used to determine the presence or absence of the analyte. The analyte is preferably a small molecule insofar as the assay is ideally suited for such a molecule, although the present invention is not limited thereto. The term "small molecule" used herein is a term of the art and is used to distinguish the molecule from macromolecules such as proteins and nucleic acids. A small molecule is often referred to in the field of immunoassays as a "hapten", being a small molecule which, when attached to a large carrier such as a protein can elicit an immune response and includes molecules such as hormones and synthetic drugs. A small molecule of this type will typically have a molecular weight of 2,000 or less, often 1,000 or less and even 500 or less. The reagent may be adapted to bind to the analyte itself, although the analyte can undergo a chemical reaction or initial complexing event before binding to the reagent. For example, the analyte might be protonated/deprotonated in the pH of the assay conditions, or after binding to a second reagent, such as a labelled antibody. Thus, the analyte which is bound to the reagent may be analyte itself or a derivative of the analyte; both are included within the scope of the present invention.

The sample which may or may not contain the analyte of interest will generally be a fluid sample and usually a biological sample (hence aqueous), such as a bodily fluid, e.g. blood, plasma, saliva, serum or urine. The sample may contain suspended particles and may even be whole blood. An advantage of the method of the present invention is that the assay may be performed on a sample which does contain suspended particles without unduly influencing the results of the assay. The sample will typically be in the order of microlitres (e.g. 1-100 µL, preferably 1-10 µL). In order to hold a fluid sample, the transducer is preferably located in a sample chamber and more preferably a well. In a preferred embodiment, the transducer is integral with the chamber, i.e. it forms one of the walls which define the chamber. The sample may simply be retained by surface tension forces, for example, inside a capillary channel.

The apparatus described herein may take the form of a hand-held portable reader and a disposable sensor containing the transducer. The sample is collected in an essentially closed system, mixed with any other reagents and placed in a reader that would perform the irradiation of the sample and detection of the resultant electrical signal.

EXAMPLES

Example 1

Preparation of Active Piezo/Pyrofilm Biosensors

A poled piezoelectric polyvinylidene fluoride (PVDF) bimorph film, coated in indium tin oxide used as the sensing device in the following examples, was conformally coated with parylene C of nominal thickness 500 nm by methods known to those skilled in the art (see for example R. Wood, 2000, To Protect and Preserve, Materials World, Vol. 8, No. 6, pp. 30-32) in a Model PDS 2010 LABCOTER® 2 coater (Specialty Coating Systems, Indianapolis, Ind., USA). This was then coated in polystreptavidin solution (200 µg/mL in PBS—10 mmol/L phosphate buffer containing 2.7 mmol/L KCl, 137 mmol/L NaCl and 0.05% Tween) by incubation at room temperature overnight. Polystreptavidin was prepared as described by Tischer et al (U.S. Pat. No. 5,061,640).

To prepare a "capture" surface, the polystreptavidin surface was incubated with biotinylated anti-TSH (thyroid stimulating hormone), giving an antibody coated surface. 10 ug/mL of biotinylated anti-TSH (Anti-TSH 5409 SPTNE-5, product code: 100034; Medix Biochemica, Kauniainen, Finland) in PBS (biotinylated by the method described below) was incubated at room temperature overnight and then washed with excess PBS and coated with Stabilcoat® (SurModics Inc, Eden Prairie, Minn., USA) before drying at 40° C.

The antibody was biotinylated by methods known to those skilled in the art. For example, a 5 mg/mL solution of antibody in PBS (NaCl 150 mmol/L, phosphate 20 mmol/L, pH 7.5) is prepared by dissolving lyophilised antibody, or by dilution. If this solution contains other proteins or Tris(trishydroxymethylaminomethane) or other interfering agents, purify by dialysis or gel filtration. Then prepare an NHS-biotin solution at 20 mmol/L in anhydrous DMSO and add 15 µL of the solution of NHS-biotin to the antibody (1 mL). Incubate for 1 hour at room temperature and then dialyse the antibody against PBS containing sodium azide (0.01%). The biotinylated antibody can be diluted to 1 mg/mL with 0.1% sodium azide and 20% of glycerol for storage at −20° C. or +4° C. The level of biotinylation should be in the range of 1-3 biotins per IgG. This can be estimated by quantitation of biotins or for high biotinylation rates, by a differential quantitation of amines. The resulting sensor is shown in FIG. 3.

Sensors on plasma-etched "clean" ITO and air-exposed "dirty" ITO piezofilm bimorphs were also prepared (exactly as described above) in order to compare with the parylene C-coated piezofilm. The XPS spectra of these substrates have already been discussed hereinabove with reference to FIGS. 4-6.

Example 2

Preparation of the Reporter Conjugates

Carbon-labelled reporter conjugates were prepared essentially as described by Van Doom et al. (U.S. Pat. No. 5,641, 689). To prepare antibody coated reporter conjugates, 1 mL of Special Black-4 RCC nominally 150 nm carbon particles (Degussa, Essen, Germany) in 5 mmol/L phosphate buffer, pH 6.2 was incubated with 200 µg/mL polystreptavidin solution overnight at room temperature with shaking, resulting in a streptavidin-coated surface (A1). The resultant carbon conjugate was washed (by centrifugation, pelleting and resuspension). 10 µg/mL of biotinylated reporter secondary monoclonal antibodies (Anti-TSH 5407 SPTN-1, product code: 100032; Medix Biochemica, Kauniainen, Finland, biotinylated as described above), reactive against TSH, in PBS was then incubated overnight with 1 mL of this streptavidin-coated carbon particle suspension with shaking. The resultant carbon conjugate was washed (by centrifugation, pelleting and resuspension) 3 times with 0.05 mol/L borate buffer at pH 8.5 and stored in this buffer in the dark at 4° C.

Example 3

Assay-Antibody-coated Piezo/Pyrofilm Sensor

Figure 9:
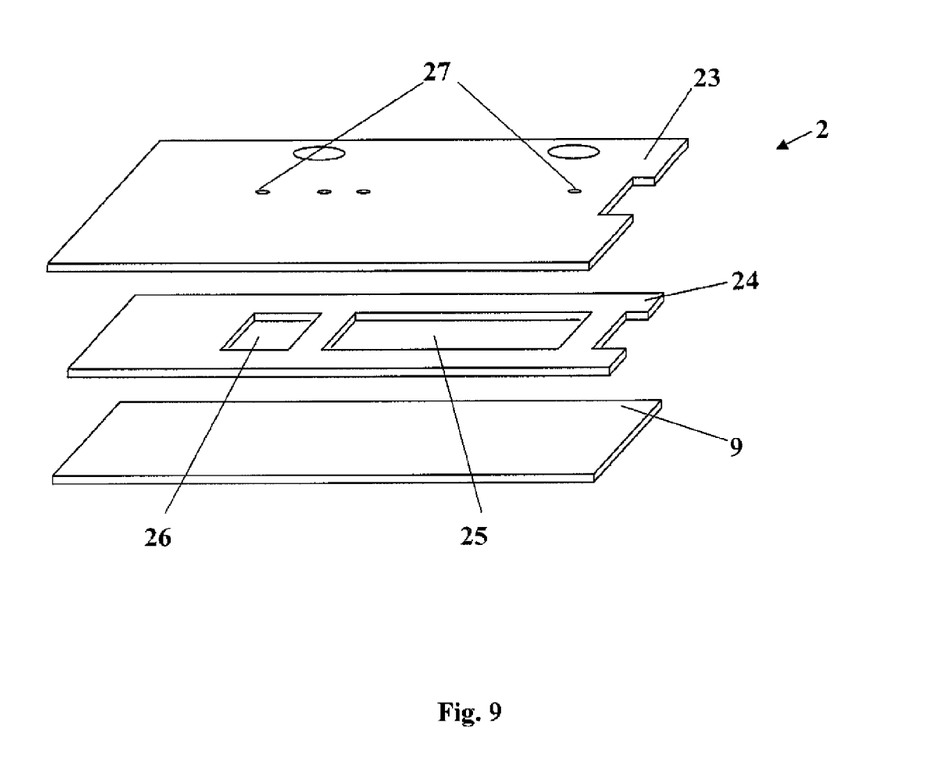
FIG. 9 shows the sensor of the present invention.

As shown in FIG. 9, a device 22 was fabricated to perform the assay. The device 22 was fabricated from a piece of antibody-coated piezofilm 9 (described hereinabove) and a piece of transparent polycarbonate lidding film 23. The films are spaced at a distance of approximately 500 microns using a spacer 24 composed of a piece of pressure sensitive adhesive-coated polyester film die-cut to form two unequally sized chambers 25,26; one chamber 25 of approximate dimensions 30×10×0.5 mm for the assay reaction and a second smaller chamber 26 of dimensions 10×10×0.5 mm for a control reaction. Provision is made to allow for electrical connections to the top and bottom surfaces of the piezofilm in order to detect the charge generated.

Figure 10:
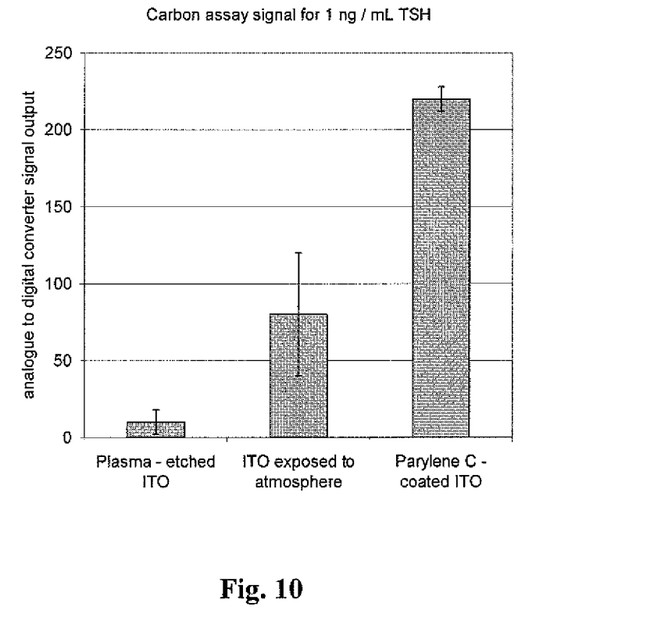
FIG. 10 shows the optically stimulated piezofilm assay performance for 1 ng/mL TSH using carbon particles in PBS buffer (error bars=1 standard deviation, number of repeats=12).

Assays are carried out by filling the larger chamber 25 (through a fill hole 27) with a mixture of 0.1 mol/L Tris buffer, containing 0.150 mol/L $MgCl_2$ and 0.075% Tween 20 solution, containing 150 nm colloidal carbon particles (at a final concentration of 0.0025% solids) coated with biotinylated antibody (as described hereinabove), reactive against TSH, and TSH standards in PBS to give a final TSH concentration of 1 ng/mL. The control chamber 26 is simultaneously filled with an identical reaction mix to that in the assay chamber with the TSH standard replaced with PBS. The entry and exit holes are sealed and the chamber assembly is connected to a test instrument such that the piezofilm 3 is oriented vertically on the side face of the chamber (although other orientations are possible). The piezofilm is then illuminated with chopped LED light sequentially with four LEDs (of wavelength 625 nm), of which three illuminate different areas of the surface of the assay chamber and one illuminates the piezofilm surface of the control chamber. For each LED pulse, a voltage is measured across the piezofilm using a lock-in amplifier and analogue to digital (ADC) converter. In the reaction chamber, the presence of the TSH leads to carbon particles binding to the piezofilm under diffusion control, leading to a growth in signal over time. In the negative control chamber, the absence of TSH means that no carbon binding to the surface is observed. The ADC signal is plotted over time and the slope of the signal over time is used as a measure of the TSH concentration. This experiment is repeated 12 times to generate a mean value and a standard deviation. This experiment was repeated using the parylene C surfaces, the "clean" ITO sensors and the "dirty" ITO sensors. The average signal (expressed in counts/min×20) along with a one standard deviation error bar is presented in FIG. 10.

The invention claimed is:
1. A sensor for use in detecting an analyte in a sample, the sensor comprising:
a source of electromagnetic radiation configured to generate a series of pulses of electromagnetic radiation;

a transducer including a pyroelectric or piezoelectric polymer substrate and a transparent electrode layer on a surface of the substrate, wherein the transducer is configured to convert energy generated by a label that undergoes non-radiative decay after absorbing the electromagnetic radiation into an electrical signal;

a layer of parylene on the transparent electrode layer;

a reagent immobilised on the transducer, the reagent having a binding site which is capable of binding the analyte or a derivative of the analyte;

a layer of protein between the parylene layer and the immobilised reagent, wherein the protein is adsorbed directly on the parylene layer by non-covalent interactions; and a detector for detecting the electrical signal from the transducer.

2. A sensor as claimed in claim 1, wherein the parylene layer has a thickness of 10 nm to 100 μm.

3. A sensor as claimed in claim 1, wherein the parylene is selected from parylene N, parylene C, parylene D, parylene F and parylene VT-4.

4. A sensor as claimed in claim 1, wherein the pyroelectric or piezoelectric polymer substrate is a polyvinyl idene fluoride film.

5. A sensor as claimed in claim 1, wherein transparent electrode layer is an indium tin oxide layer.

6. A sensor as claimed in claim 4, wherein the transducer is an indium tin oxide-coated polyvinyl idene fluoride film.

7. A sensor as claimed in claim 1, wherein the reagent is an antibody, or a nucleic acid or an analogue thereof.

8. A sensor as claimed in claim 1, further comprising a sample chamber for holding the sample in contact with the transducer.

9. A sensor as claimed in claim 1, wherein the detector is adapted to determine the time delay between each pulse of electromagnetic radiation from the radiation source and the generation of the electrical signal.

* * * * *